(12) United States Patent
Park et al.

(10) Patent No.: US 9,121,830 B2
(45) Date of Patent: Sep. 1, 2015

(54) SPECTROMETER APPARATUS USING CONTINUOUS WAVE LASER AND PHOTOMULTIPLIER TUBE

(75) Inventors: Kihong Park, Gwanju (KR); Ji-Hyun Kwak, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 0 days.

(21) Appl. No.: 13/325,808

(22) Filed: Dec. 14, 2011

(65) Prior Publication Data

US 2012/0327395 A1  Dec. 27, 2012

(30) Foreign Application Priority Data

Jun. 21, 2011 (KR) ........................ 10-2011-0060040

(51) Int. Cl.
*G01J 3/30* (2006.01)
*G01N 21/71* (2006.01)

(52) U.S. Cl.
CPC .................... *G01N 21/718* (2013.01)

(58) Field of Classification Search
CPC .................................................... G01N 21/718
USPC ........................................................ 356/300
See application file for complete search history.

(56) References Cited

U.S. PATENT DOCUMENTS

| | | | |
|---|---|---|---|
| 4,383,171 A * | 5/1983 | Sinha et al. | 250/282 |
| 4,779,028 A * | 10/1988 | Blair | 315/367 |
| 8,398,839 B1 * | 3/2013 | Morales et al. | 204/547 |

FOREIGN PATENT DOCUMENTS

CN        1481575 A        3/2004

* cited by examiner

*Primary Examiner* — Tarifur Chowdhury
*Assistant Examiner* — Omar Nixon
(74) *Attorney, Agent, or Firm* — Nath, Goldberg & Meyer; Jerald L. Meyer

(57) ABSTRACT

Disclosed is a spectrometer apparatus using a continuous wave laser and a photomultiplier tube. The spectrometer apparatus includes a continuous wave laser irradiating part to irradiate a continuous wave laser to introduced particles, a scattering light measuring part to measure a scattering light emitted from the particles due to the continuous wave laser, a triggering signal generator to generate a triggering signal if a measurement value of the scattering light measuring part is greater than a preset value or equal to the preset value, a pulse laser irradiating part to receive the triggering signal to irradiate a pulse laser to the particles, and a spectral analysis part to measure an emission light generated from the particles due to the pulse wave laser to analyze elements consisting of the particles.

7 Claims, 3 Drawing Sheets

SPECTROMETER APPARATUS USING CONTINUOUS WAVE LASER AND PHOTOMULTIPLIER TUBE

CROSS-REFERENCE TO RELATED APPLICATION

This application claims the benefit under 35 U.S.C. §119 of Korean Patent Application No. 10-2011-0060040, filed on Jun. 21, 2011 in the Korean Intellectual Property Office, the entirety of which is incorporated herein by reference.

BACKGROUND OF THE INVENTION

1. Field of the Invention

The present invention relates to a spectrometer apparatus using a continuous wave laser and a photomultiplier tube.

2. Description of the Related Art

Conventionally, according to the real-time measurement of a single particle in atmospheric fine particle using a LIBS (Laser-Induced Breakdown Spectroscopy is reported by G. A. Lithgow et al. ("Ambient measurements of metal-containing PM2.5 in an urban environment using laser-induced breakdown spectroscopy", Atmos. Environ. 38, 3319-3328, 2004) and Carranza et al. ("On-line analysis of ambient air aerosols using laser-induced breakdown spectroscopy", Spectrochim. Part B. 56, 851-864, 2001), particles have been measured through a free-firing mode in which the path of fine particle floating at the air is centralized by a focusing nozzle and then a high-frequency laser (in general, a 10 Hz-laser) is irradiated onto the fine particle. However, in such a mode, since hitting efficiency representing exact hitting of fine particle by a laser is very low, a LIBS spectrum for the single particle is obtained only in a part of several thousand shots. Accordingly, particle measurement efficiency is degraded, and the unnecessary blank spectrum occupies the most part of data. In addition, when a specific event (Asian Dust event or local pollution event) occurs, the particle measurement according to the free-firing mode may be not effective when quickly detecting particles or distinguishing between particles.

SUMMARY OF THE INVENTION

Accordingly, the present invention has been made keeping in mind the above problems occurring in the related art, and an object of the present invention is to provide a technology to irradiate a pulse laser onto only particles having a preset particle size or more by controlling the irradiation of a pulse laser when a fine particle is measured.

Another object of the present invention is to provide a technology to measure an emission light of fine particles by irradiating a pulse laser onto the fine particles, so that the elements constituting of the fine particles are detected.

However, objects of the present invention are not limited to the above object, but those skilled in the art can infer other objects from the following description.

In order to accomplish the above objects of the present invention, there is provided a spectrometer apparatus including a continuous wave laser irradiating part to irradiate a continuous wave laser to introduced particles, a scattering light measuring part to measure a scattering light emitted from the particles due to the continuous wave laser, a triggering signal generator to generate a triggering signal if a measurement value of the scattering light measuring part is greater than a preset value or equal to the preset value, a pulse laser irradiating part to receive the triggering signal to irradiate a pulse laser to the particles, and a spectral analysis part to measure an emission light generated from the particles due to the pulse laser to elemental composition consisting of the particles.

Preferably, the scattering light measuring part includes a photo-multiplier tube receiving the scattering light, converting the scattering light to an electrical signal, and amplifying the electrical signal, and an oscilloscope receiving the amplified electrical signal and calculating a voltage value based on the amplified electrical signal.

Preferably, the triggering signal generator applies the triggering signal to the pulse laser irradiating part if the voltage value calculated in the oscilloscope is greater than or equal to the preset value.

Preferably, the triggering signal generator applies the triggering signal to the pulse laser irradiating part in timing variably set according to a degree of the voltage value exceeding the preset value.

Preferably, the continuous wave laser irradiating part may irradiate the continuous wave laser in a direction perpendicular to a travelling direction of the particles.

Preferably, a contact point between the particles and the pulse laser irradiated from the pulse laser irradiating part may be spaced apart from a contact point between the particles and the continuous wave laser by a preset distance.

Preferably, the pulse laser irradiating part may irradiate the pulse laser from a direction opposite to a travelling direction of the particles.

In addition, preferably, the pulse laser irradiating part may include a focusing lens provided on a travelling path of the pulse laser to focus the pulse laser and irradiate the pulse laser to the particles.

In addition, according to the present invention, the continuous wave irradiated from the continuous wave laser irradiating part may have a wavelength of about 640 nm, and the pulse laser irradiated from the pulse laser irradiating part may have a wavelength of about 1064 nm.

As described above, according to the present invention, since the pulse laser is irradiated onto only fine particles having a preset particle size or more, hitting efficiency, in which the pulse laser hits the fine particle, is improved so that the efficiency in particle measurement can be improved.

In addition, according to the present invention, since the irradiation of the pulse laser is controlled, spectral data of unnecessary fine particles can be reduced.

In addition, according to the present invention, when a specific event (yellow sand phenomenon or local pollution) occurs, the fine particles can be rapidly detected and distinguished.

DETAILED DESCRIPTION OF THE INVENTION

Figure 1:
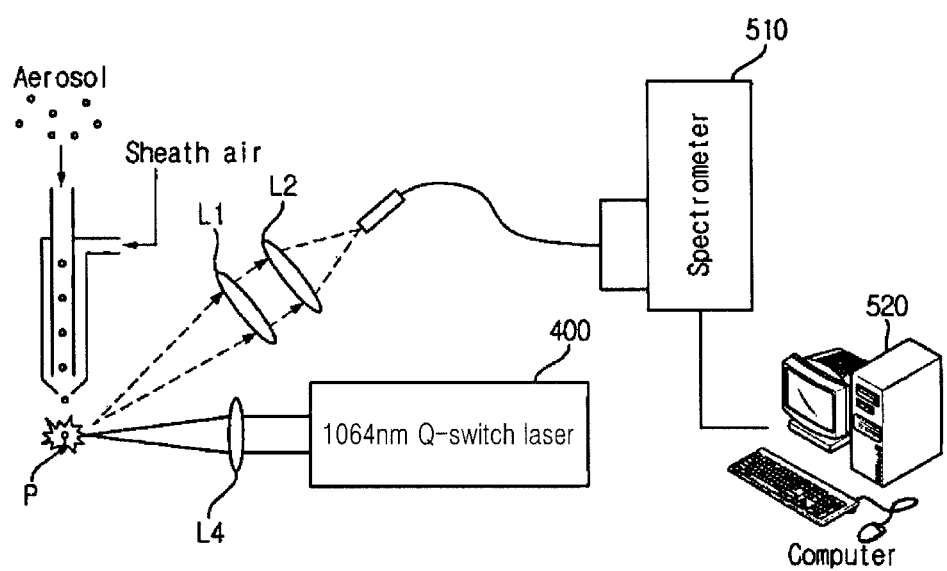
FIG. 1 is a view showing a spectrometer apparatus according to the related art.

Hereinafter, exemplary embodiments of the present invention will be described in detail with reference to accompanying drawings. In the following description, when one component is connected to another component, this means not only that one component is directly connected to another component, but also that one component is connected to another component while interposing the third component between one component and another component. In addition, when reference numerals are assigned to components in the accompanying drawings, the same reference numerals must be assigned to the same components although the components are shown in different drawings. In addition, the construction and the operation of the present invention shown in the accompanying drawings and described with reference to the accompanying drawings will be described as at least one embodiment, and the technical spirit, the main components, and the operation of the present invention are not limited to the embodiment.

Prior to the detailed description about the present invention, a spectrometer apparatus according to the related art and a method for performing spectral analysis of fine particles by using the same will be described. The spectrometer apparatus according to the related art and the method for performing spectral analysis of fine particles by using the same are not within the scope of the present invention, but allow those skilled in the art to clearly comprehend the present invention through contrast explanation.

The spectrometer apparatus according to the related art will be described with reference to FIG. 1

FIG. 1 is a view showing the spectrometer apparatus according to the related art.

As shown in FIG. 1, the spectrometer apparatus according to the related art includes a 1064 nm Q-switch laser 400, a spectrometer 510, and a computer 520. Fine particles P are introduced into a particle injector including inner and outer nozzles. The particle injector has the outer nozzle provided at the outside of the inner nozzle serving as a passage through which the fine particles P flow. The outer nozzle allows sheath air to flow therethrough, so that the fine particles P can flow through the inner nozzle while being centralized.

The 1064 nm Q-switch laser 400 irradiates a pulse laser onto the fine particles P flowing out of the inner nozzle through the inner nozzle. In detail, the 1064 nm Q-switch laser 400 irradiates a pulse laser having a wavelength of 1064 nm. A focusing lens L4 is placed at the front of the 1064 nm Q-switch laser 400 to focus the pulse laser and irradiate the pulse laser to the fine particles P.

If the pulse laser is irradiated onto the fine particles P, high-temperature plasma is produced, so that the fine particles P atomized or ionized under the plasma come into the excited state and then drop into a ground state. The spectrometer 510 measures an emission light when the fine particles P are dropped into the ground state from the excited state, thereby analyzing elements consisting of the fine particles P.

In the spectrometer apparatus according to the related art, when a pulse laser is irradiated onto the fine particles P, a pulse laser having a frequency of about 10 Hz is irradiated through a free-firing mode. Therefore, since the probability of hitting the fine particles P by the pulse laser is very low, the spectrum for fine particles can be obtained only by a part of several hundred laser shots. Accordingly, the efficiency to measure the fine particles P is lowered, so that undesirable blank spectrum data may be produced.

Hereinafter, the present invention suggested to solve the problem will be described.

A spectrometer apparatus according to one embodiment of the present invention will be described with reference to FIGS. 2 and 3.

Figure 2:
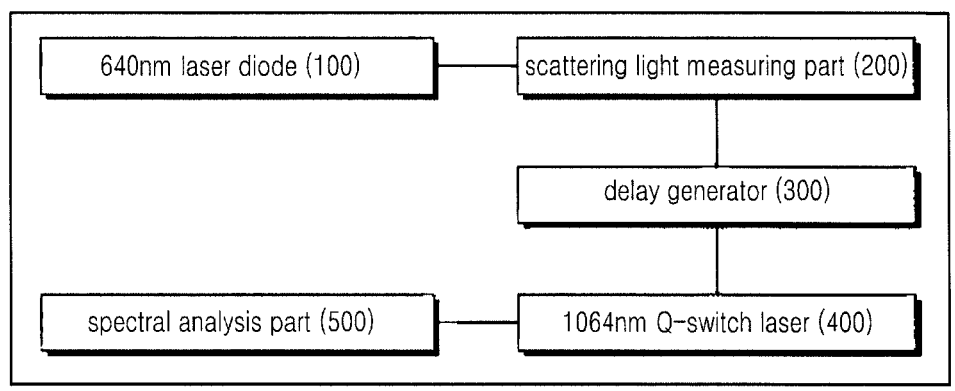
FIG. 2 is a block diagram used to explain a spectrometer apparatus according to one embodiment of the present invention.

FIG. 2 is a block diagram used to explain a spectrometer apparatus 10 according to one embodiment of the present invention.

As shown in FIG. 2, the spectrometer apparatus 10 according to one embodiment of the present invention includes a 640 nm laser diode 100, a scattering light measuring part 200, a delay generator 300, a 1064 nm Q-switch laser 400, and a spectral analysis part 500.

The 640 nm laser diode 100 irradiates a continuous wave laser onto introduced particles. In this case, the particles include fine particles, and the fine particles are introduced into the spectrometer apparatus 10 from a particle injector including inner and outer nozzles as described in the related art. The 640 nm laser diode 100 irradiates a continuous wave laser onto the introduced fine particles, so that a scattering light can be emitted from the fine particles.

The scattering light measuring part 200 measures the scattering light emitted from the fine particles due to the continuous wave laser. In this case, the scattering light measuring part 200 includes a photomultiplier tube (PMT) (see 210 of FIG. 3) and an oscilloscope (see 220 of FIG. 3). The photomultiplier tube converts the scattering light received therein into an electrical signal and amplifies the electrical signal. The oscilloscope receives the amplified electrical signal to calculate a voltage value based on the electrical signal.

The delay generator 300 generates a triggering signal if a measurement value of the scattering light measuring part 200 is greater than or equal to a preset value. In detail, the delay generator 300 generates the triggering signal if the voltage value calculated in the oscilloscope is greater than or equal to the preset value. In other words, since the voltage value calculated from the oscilloscope is affected by the particle size of the fine particles, a high voltage value refers to that the size of the fine particles is large. Therefore, the lower limit size of the fine particles is set and a voltage value corresponding to the lower limit size of the fine particles is set, so that the triggering signal is generated only if the fine particles having the preset particle size or more are taken.

The 1064 nm Q-switch laser 400 receives the triggering signal to irradiate a pulse laser onto the fine particles. In other words, the pulse laser generated from the 1064 nm Q-switch laser 400 is irradiated onto the fine particles only if the voltage vale calculated in the oscilloscope of the scattering light measuring part 200 is greater than or equal to the preset value.

The spectral analysis part 500 measures an emission light derived from the particles colliding with the pulse laser of the 1064 nm Q-switch laser 400 to analyze elements consisting of the particles. Since the spectral analysis part 500 has the same components as those of spectrometer spectral analysis part according to the related art, the details thereof will be omitted.

Hereinafter, the description about the realization and the operating procedure of the spectrometer apparatus according to one embodiment of the present invention will be disclosed.

Figure 3:
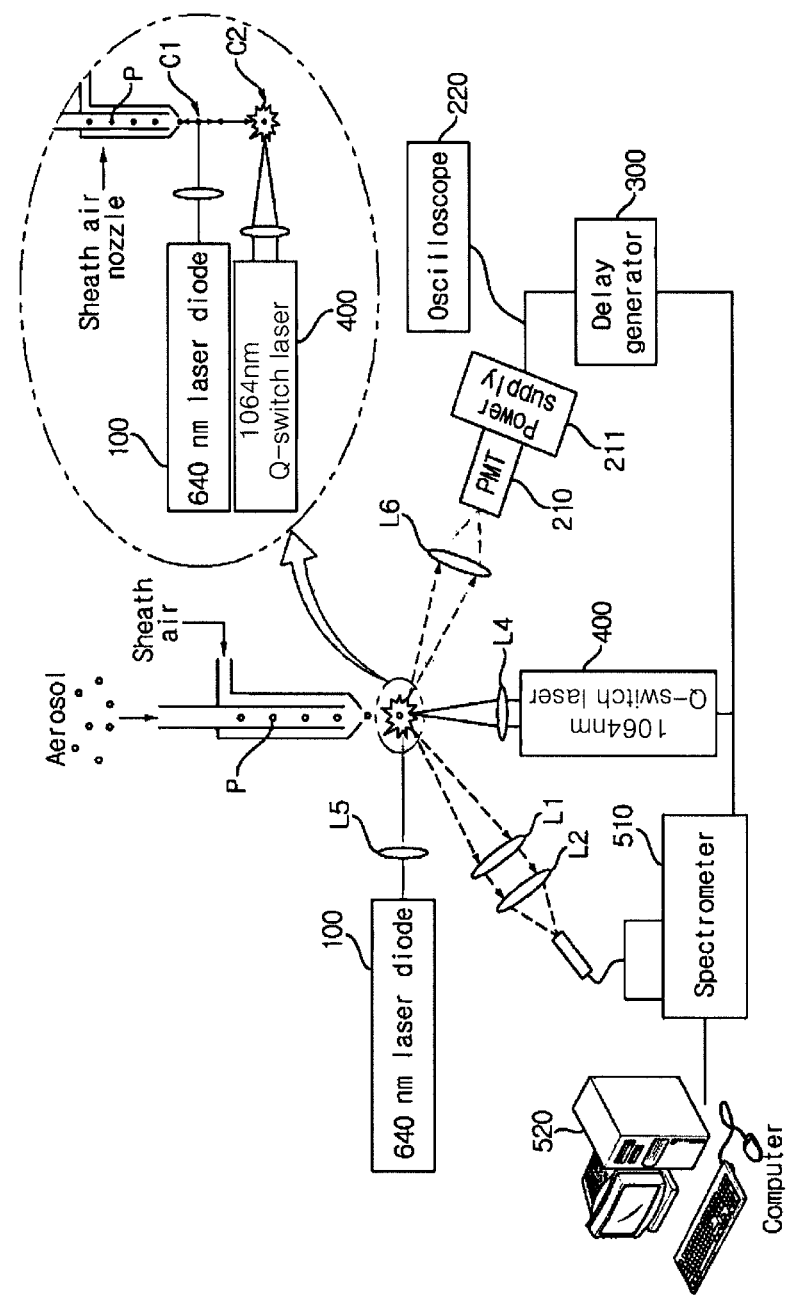
FIG. 3 is a view used to explain the realization of the spectrometer apparatus according to one embodiment of the present invention.

FIG. 3 is a view used to explain the realization of the spectrometer apparatus according to one embodiment of the present invention.

Referring to FIG. 3, the fine particles P are introduced from the particle injector. Since the particle injector has been described above, the details thereof will be omitted. The continuous wave laser is irradiated onto the fine particles P, which are introduced from the particle injector, from the 640 nm laser diode 100. Preferably, the 640 nm laser diode 100 is realized by using a laser diode to generate a continuous wave having a wavelength of about 640 nm. In addition, preferably, the 640 nm laser diode 100 irradiates the continuous wave laser in a direction perpendicular to a travelling direction of the fine particles P. In other words, the 640 nm laser diode 100 irradiates the continuous wave laser from the lateral side toward the travelling direction of the fine particles P on the basis of FIG. 3. In addition, preferably, the focusing lens L5 is provided at the front of the 640 nm laser diode 100, so that the focused continuous wave laser can be irradiated onto the fine particles P.

If the fine particles P are hit by the continuous wave laser, the fine particles P emit the scattering light. The scattering light is measured by the scattering light measuring part 200. In detail, the scattering light is converted to an electrical signal through photoelectric conversion in the PMT 210 of the scattering light measuring part 200. Although a power supply 211, which supplies power to the PMT 210, is shown in FIG. 3 separately from the PMT 210, the power supply 211 may be embedded in the PMT 210 so that the power supply 211 may be formed integrally with the PMT 210. In addition, a focusing lens L6 to focus the scattering light is preferably provided at the front of the PMT 210.

The amplified electrical signal is transferred to the oscilloscope 220. The oscilloscope 220 calculates a voltage value based on the electrical signal.

The delay generator 300 receives the voltage value calculated in the oscilloscope 220 and applies the triggering signal to the 1064 nm Q-switch laser 400 if the voltage value is greater than or equal to the preset value. In this case, the preset value is a voltage value set to select fine particles to be measured. As described above, the preset value is a value set based on the fact that a voltage value calculated in the oscilloscope varies according to particle sizes of the fine particles.

Meanwhile, preferably, the timing to apply the triggering signal generated from the delay generator 300 to the 1064 nm Q-switch laser 400 is variably set according to the degree of the measured voltage value exceeding the preset value. In other words, the oscilloscope 220 calculates a greater voltage value as a fine particle P has a larger size. Accordingly, preferably among fine particles P causing the voltage value greater than the preset value, the timing to generate the triggering signal is set faster in the case of fine particles causing a greater voltage value than the timing to generate the triggering signal in the case of fine particles causing a less voltage value.

This is necessary to exactly adjust a focal length of a laser irradiated onto a fine particle P in the state that the position of the 1064 nm Q-switch laser 400 is fixed because the fine particle P is dropped at a higher velocity as the size of the fine particle P is increased.

The 1064 nm Q-switch laser 400 irradiates a pulse laser onto a fine particle P only if the triggering signal described above is applied to the 1064 nm Q-switch laser 400. In other words, since the triggering signal is generated due to the scattering light emitted from the fine particle P having a specific size or more, the pulse laser is irradiated onto only the fine particle P having the specific size or more. In detail, the 1064 nm Q-switch laser 400 generates a pulse wave having a wavelength of 2064 nm. In addition, preferably, the focusing lens 400 is provided at the front of the 1064 nm Q-switch laser 400 to focus the pulse laser and irradiate the pulse laser onto the fine particle P. In this case, referring to an enlarged part (dotted circular part) of FIG. 3, a contact point C2 between a pulse laser generated from the 1064 nm Q-switch laser 400 and a fine particle P is spaced apart from a contact point C1 between a continuous wave laser generated from the 640 nm laser diode 100 and a fine particle P by a predetermine distance. Preferably, the 1064 nm Q-switch laser 400 is placed below the position of the 640 nm laser diode 100 in the travelling direction of fine particles P.

Meanwhile, the 640 nm laser diode 100 is preferably installed in such a manner that the 640 nm laser diode 100 irradiates a continuous wave laser from the lateral side perpendicular to the travelling direction of fine particles P on the basis of FIG. 3 because the 640 nm laser diode 100 must irradiate the continuous wave laser onto all fine particles P. In addition, the 1064 nm Q-switch laser 400 preferably faces the travelling direction of the fine particles P because the 1064 nm Q-switch laser 400 irradiates a pulse wave onto one specific fine particle. In addition, similarly to the 640 nm laser diode 100, the 1064 nm Q-switch laser 400 is preferably installed at a place perpendicular to the travelling direction of the fine particles P.

If the pulse laser is irradiated onto fine particles P, high-temperature plasma is produced, so that the fine particles P atomized or ionized under the plasma come into an excited state and drop into a ground state after an excited state. The spectrometer 510 measures an emission light when the particles P drop into the ground state from the excited state, thereby qualitatively and quantitatively analyzing elements consisting of the fine particles P. Those skilled in the art can comprehend the chemical analysis of elements performed by the spectrometer based on a generally-known technology, and the chemical analysis of elements performed by the spectrometer is not within the scope of the present invention. Accordingly, the details thereof will be omitted. Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A spectrometer apparatus comprising:
   a continuous wave laser irradiating part configured to irradiate a continuous wave laser to introduced particles;
   a scattering light measuring part configured to measure a scattering light emitted from the particles due to the continuous wave laser, wherein the scattering light measuring part comprises
      a photo-multiplier tube configured to receive the scattering light, convert the scattering light to an electrical signal, and amplify the electrical signal, and
      an oscilloscope configured to receive the amplified electrical signal and calculate a voltage value based on the amplified electrical signal;
   a triggering signal generator configured to generate a triggering signal if the voltage value calculated in the oscilloscope within the scattering light measuring part is greater than a preset voltage value or equal to the preset voltage value;
   a pulse laser irradiating part configured to receive the triggering signal to irradiate a pulse laser to the particles, wherein,
      the triggering signal generator applies the triggering signal to the pulse laser irradiating part if the voltage value calculated in the oscilloscope is greater than or equal to the preset voltage value; and
   a spectral analysis part configured to measure an emission light generated from the particles due to the pulse laser to analyze elements consisting of the particles,
   wherein a timing to apply the triggering signal to the pulse laser irradiating part is variably set according to a degree of the voltage value exceeding the preset voltage value, and
   wherein the timing of a particle causing a greater voltage value is set faster than the timing of a particle causing a less voltage value.

2. The spectrometer apparatus of claim 1, wherein the continuous wave laser irradiating part irradiates the continuous wave laser in a direction perpendicular to a travelling direction of the particles.

3. The spectrometer apparatus of claim 2, wherein a contact point between the particles and the pulse laser irradiated from the pulse laser irradiating part is spaced apart from a contact point between the particles and the continuous wave laser by a preset distance.

4. The spectrometer apparatus of claim 2, wherein the pulse laser irradiating part irradiates the pulse laser from a direction opposite to a travelling direction of the particles.

5. The spectrometer apparatus of claim 3, wherein the pulse laser irradiating part includes a focusing lens provided on a travelling path of the pulse laser to focus the pulse laser and irradiate the pulse laser to the particles.

6. The spectrometer apparatus of claim 1, wherein the continuous wave irradiated from the continuous wave laser irradiating part has a wavelength of about 640 nm, and the pulse laser irradiated from the pulse laser irradiating part has a wavelength of about 1064 nm.

7. A method of spectrometry, comprising:
   introducing particles into a spectrometer apparatus;
   continuously irradiating the introduced particles via a continuous wave laser;
   measuring a scattering light emitted from the particles due to the continuous wave laser via a scattering light measuring part;
   generating a triggering signal via a triggering signal generator when a calculated voltage value by an oscilloscope in the scattering light measuring part is greater than a preset voltage value or equal to a preset voltage value;
   irradiating the introduced particles via a pulse laser upon receiving the triggering signal;
   measuring an emission light generated from the particles due to the pulse laser by way of a spectral analysis part; and
   analyzing elements of the particles by way of the emitted light,
   wherein a timing to apply the triggering signal is variably set according to a degree of the voltage value exceeding the preset voltage value, and
   wherein the timing of a particle causing a greater voltage value is set faster than the timing of a particle causing a less voltage value.

* * * * *